(12) United States Patent
Schmied et al.

(10) Patent No.: US 11,399,806 B2
(45) Date of Patent: Aug. 2, 2022

(54) METHOD AND SYSTEM FOR PROVIDING FREEHAND RENDER START LINE DRAWING TOOLS AND AUTOMATIC RENDER PRESET SELECTIONS

(71) Applicant: GE Precision Healthcare LLC, Wauwatosa, WI (US)

(72) Inventors: Heinz Schmied, Zipf (AT); Helmut Brandl, Zipf (AT)

(73) Assignee: GE PRECISION HEALTHCARE LLC, Wauwatosa, WI (US)

(*) Notice: Subject to any disclaimer, the term of this patent is extended or adjusted under 35 U.S.C. 154(b) by 309 days.

(21) Appl. No.: 16/660,487

(22) Filed: Oct. 22, 2019

(65) Prior Publication Data

US 2021/0113193 A1  Apr. 22, 2021

(51) Int. Cl.
| | | |
|---|---|---|
| *G06T 11/40* | (2006.01) | |
| *A61B 8/08* | (2006.01) | |
| *A61B 8/00* | (2006.01) | |
| *G06F 3/04845* | (2022.01) | |
| *G06F 3/04883* | (2022.01) | |
| *G06F 3/04842* | (2022.01) | |

(52) U.S. Cl.
CPC ............ *A61B 8/5207* (2013.01); *A61B 8/465* (2013.01); *G06F 3/04842* (2013.01); *G06F 3/04845* (2013.01); *G06F 3/04883* (2013.01); *G06T 11/40* (2013.01); *G06T 2210/41* (2013.01)

(58) Field of Classification Search
CPC ....... A61B 8/5207; A61B 8/465; A61B 8/483; A61B 8/5215; A61B 8/54; A61B 8/466; A61B 8/0866; A61B 8/467; G06F 3/04842; G06F 3/04845; G06F 3/04883; G06F 3/03543; G06F 3/041; G06T 11/40; G06T 2210/41; G06T 15/08; G06T 11/003; G06T 2207/10132
See application file for complete search history.

(56) References Cited

U.S. PATENT DOCUMENTS

| 6,102,861 A | 8/2000 | Avila et al. |
|---|---|---|
| 6,692,441 B1 | 2/2004 | Poland et al. |

(Continued)

FOREIGN PATENT DOCUMENTS

JP   2016182454 A  * 10/2016  ........... A61B 8/0866

*Primary Examiner* — William A Beutel
(74) *Attorney, Agent, or Firm* — McAndrews, Held & Malloy, Ltd.; Jacob Groethe; David Bates (57) ABSTRACT

A system and method for providing freehand render start line drawing tools and automatic render preset selections is provided. The method includes receiving a render start line drawn in freehand via a user input device on a 2D image of a profile of a structure of interest. The method includes analyzing pixel intensity values in a region of the render start line. The method includes automatically selecting one of a plurality of sets of render mode presets based on the pixel intensity values in the region of the render start line. Each of the plurality of sets of render mode presets is associated with a different rendering mode. Each of the rendering modes is associated with a different pixel intensity value range. The method includes generating a volume rendering according to the automatically selected set of render mode presets. The method includes presenting the volume rendering at a display system.

20 Claims, 6 Drawing Sheets

(56) References Cited

U.S. PATENT DOCUMENTS

| | | | |
|---|---|---|---|
| 2003/0210254 A1* | 11/2003 | Doan | G06T 19/00 |
| | | | 345/661 |
| 2005/0119550 A1* | 6/2005 | Serra | G06T 19/00 |
| | | | 600/407 |
| 2009/0036749 A1 | 2/2009 | Freiburger et al. | |
| 2014/0075281 A1* | 3/2014 | Rubin | G06F 40/169 |
| | | | 715/230 |
| 2016/0242742 A1* | 8/2016 | Gratacos Solsona | |
| | | | G06T 7/0012 |
| 2017/0086783 A1 | 3/2017 | Denk et al. | |
| 2018/0121075 A1* | 5/2018 | Resendez Rodriguez | |
| | | | G06F 3/04845 |
| 2020/0146773 A1* | 5/2020 | Levin | A61C 5/50 |

* cited by examiner

METHOD AND SYSTEM FOR PROVIDING FREEHAND RENDER START LINE DRAWING TOOLS AND AUTOMATIC RENDER PRESET SELECTIONS

FIELD

Certain embodiments relate to ultrasound imaging. More specifically, certain embodiments relate to a method and system for providing freehand render start line drawing tools. The system may analyze the pixel space around the freehand render start line drawn by an operator to automatically select render presets applied to perform volume rendering.

BACKGROUND

Ultrasound imaging is a medical imaging technique for imaging organs and soft tissues in a human body. Ultrasound imaging uses real time, non-invasive high frequency sound waves to produce two-dimensional (2D), three-dimensional (3D), and/or four-dimensional (4D) (i.e., real-time/continuous 3D images) images.

Ultrasound imaging is a valuable, non-invasive tool for diagnosing various medical conditions. Acquired ultrasound data may be analyzed and/or processed to detect anatomical structures evaluated by a medical professional to perform the diagnosis. In some cases, volume renderings of 3D or 4D image data may provide desired views and/or assist in performing a diagnosis. For example, an operator may perform a surface rendering of a fetus to generate a volume rendering of a face of the fetus. Specific rendering modes are also available for bone, tissue, organs, and the like. Each of the different rendering modes may utilize different rendering presets and/or combinations of presets, such as surface smooth render mode, surface texture render mode, X-ray render mode, maximum transparency render mode, and the like. The different rendering modes may also have presents related to render color (e.g., sepia, HD life, etc.), render direction, render quality, and the like.

Currently, an operator performs numerous time-consuming steps to acquire a volume rendering of a structure. For example, an ultrasound operator may acquire a 2D image of a profile of the structure of interest. The operator may initiate a volume preparation mode and may set a position and size of a render box. Next, the operator may select various render presets, such as a render type (e.g., surface, bone, tissue, etc.), a render color (e.g., sepia, HD life, etc.), a render direction, a render quality, and the like. Finally, the operator may initiate the volume acquisition and rendering. The volume rendering generated based on the render box and selected presets is presented at a display.

Figure 1:
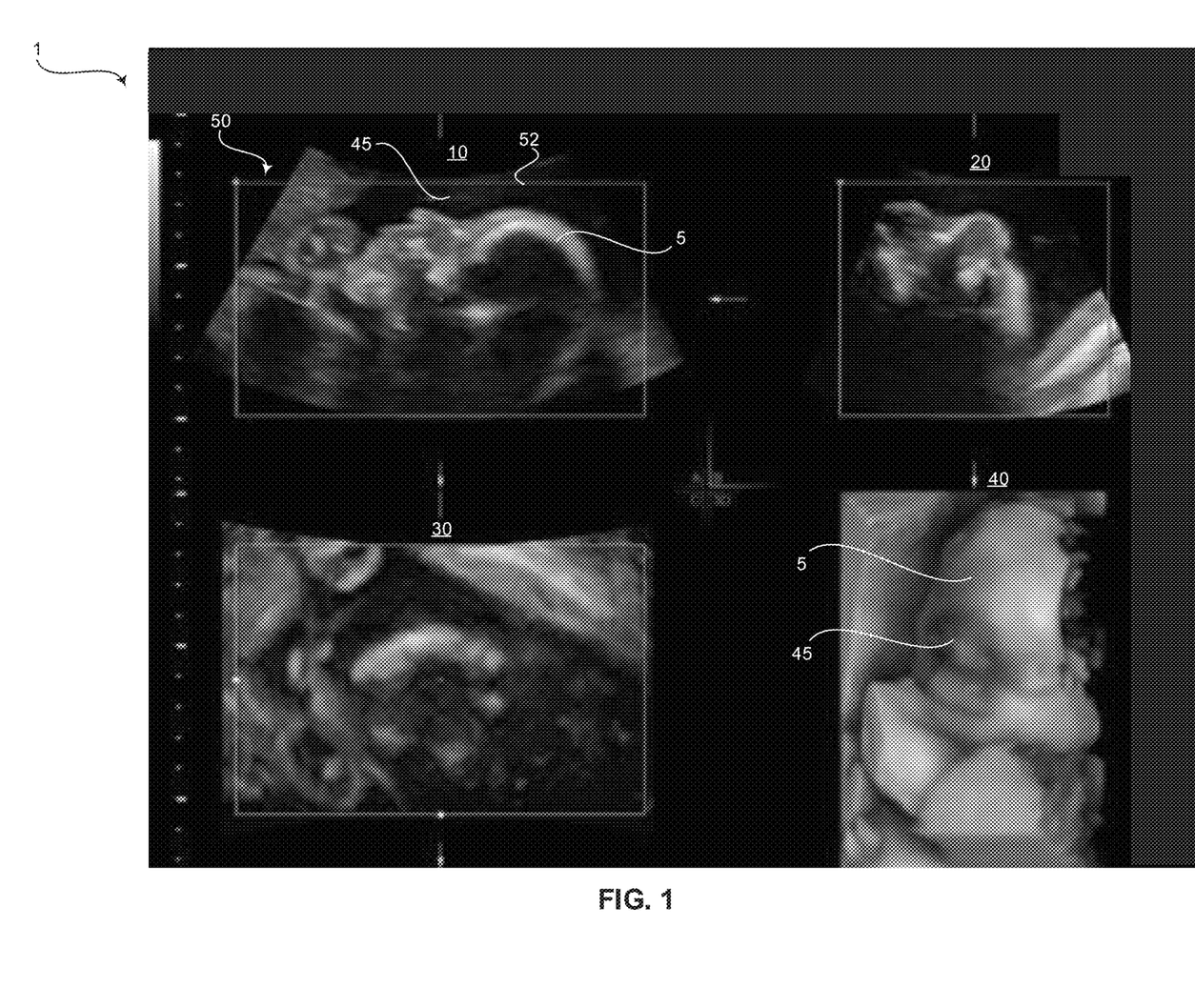
FIG. 1 is a display of a volume rendering generated based on manually selected render presets and a render box sized and positioned to surround a profile of a fetal head in a 2D image, as known in the art.

FIG. 1 is a display 1 of a volume rendering 40 generated based on manually selected render presets and a render box 50 sized and positioned to surround a profile of a fetal head 5 in a 2D image 10, as known in the art. Referring to FIG. 1, various 2D image views 10, 20, 30 and a volume rendering 40 are shown. The 2D image views 10, 20, 30 include views in an A-plane 10, B-plane 20, and C-plane 30. The A-plane image 10 illustrates an acquired profile of a fetal head 5. The render box 50 is sized and positioned to surround the fetal head. As shown in FIG. 1, the render box 50 typically includes a straight render start line 52 but may also include a render start line having a pre-defined curvature. The volume rendering 40 is generated based on presets selected by the operator after the volume preparation mode is initiated and the render box size and position is set. As described above, the typical process of generating a volume rendering is time consuming. Moreover, the volume rendering 40 may include semi-transparent structures 45, such as parts of an umbilical cord, placenta, or uterine wall, which may inadvertently be included with the rendering 40 based on an inability to exclude small structures 45 in front of the surface of the structure 5 due to the straight render start line 52 or render start line having the pre-defined curvature. For example, the surface rendering 40 of the fetal face 5 in FIG. 1 includes an obstruction 45 that makes the volume rendering 40 undesirable and otherwise unusable.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for providing freehand render start line drawing tools and automatic render preset selections, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Certain embodiments may be found in a method and system for providing freehand render start line drawing tools and automatic render preset selections. Various embodiments have the technical effect of generating a volume rendering based on a received freehand drawing of a render start line to allow an operator to avoid undesirable obstructions. Aspects of the present have the technical effect of automatically selecting render mode presets applied to generate a volume rendering, the render mode presets selected based on pixel intensity values in a region of manually drawn render start line.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 2.

Figure 2:
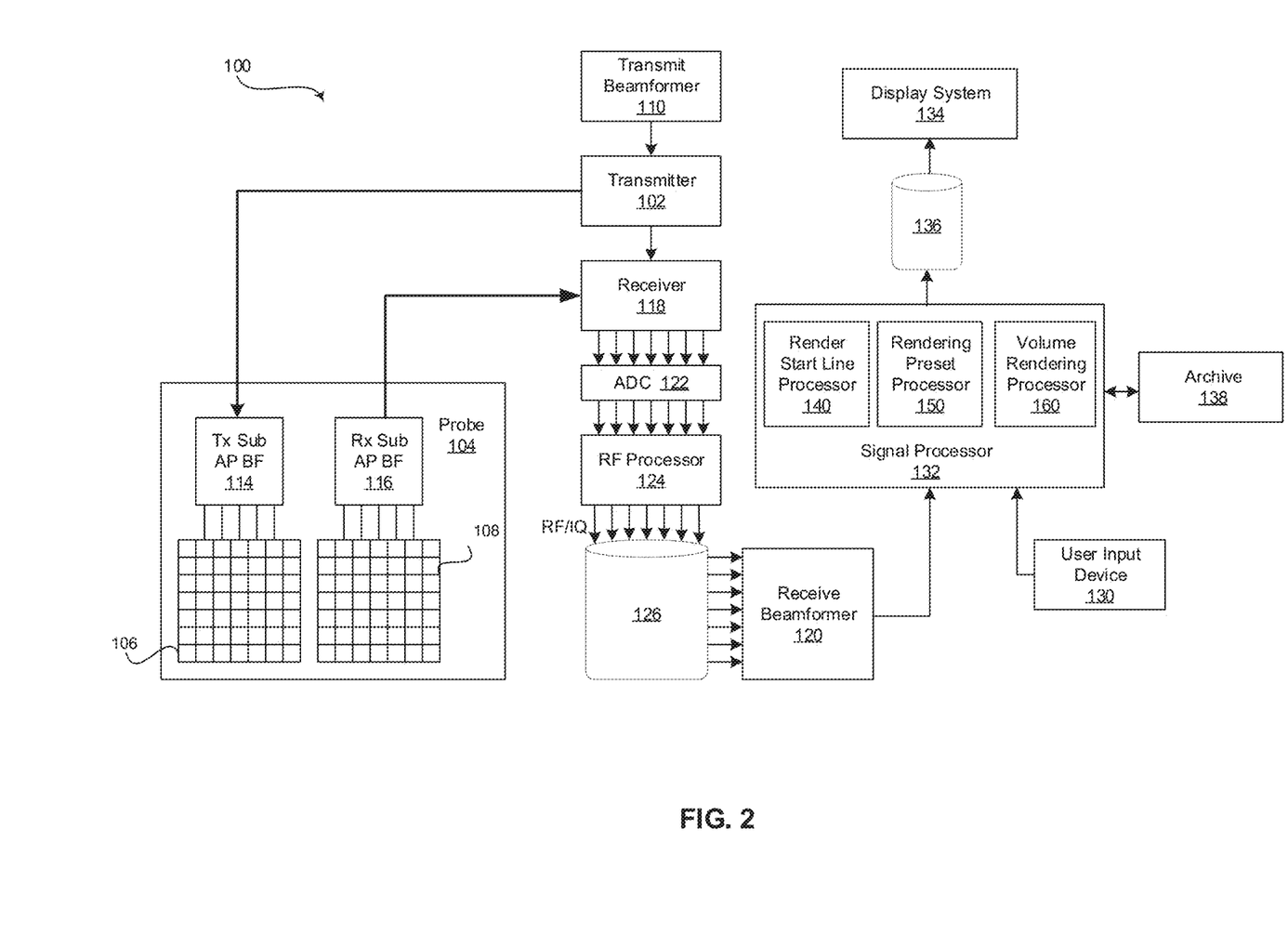
FIG. 2 is a block diagram of an exemplary ultrasound system that is operable to provide freehand render start line drawing tools and automatic render preset selections, in accordance with various embodiments.

FIG. 2 is a block diagram of an exemplary ultrasound system 100 that is operable to provide freehand render start line drawing tools and automatic render preset selections, in accordance with various embodiments. Referring to FIG. 2, there is shown an ultrasound system 100. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as a fetus, a spine, an endometrium of a uterus, a heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, rendering present parameters, initiate a volume preparation mode, provide a freehand drawing of a render start line, initiate generation of a volume rendering, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, a touch pad, a trackball, motion tracking, voice recognition, a mousing device, keyboard, camera and/or any other device capable of receiving a user directive. In certain embodiments, one or more of the user input devices 130 may be integrated into other components, such as the display system 134, for example. As an example, user input device 130 may include a touchscreen display.

In various embodiments, the user input device 130 may be operable to provide customized rendering preset parameters via a system set-up page. For example, an operator may operate the user input device 130 to alter default parameters such as a render color (e.g., sepia, HD life, etc. for a particular rendering type), combinations of render modes (e.g., mix of X-ray render mode and maximum transparency render mode, or mix of surface texture render mode and maximum transparency mode, for a bone rendering), percentages of mixed render modes (e.g., 50% surface texture render mode and 50% surface smooth render mode for a surface rendering), and the like. In certain embodiments, the user input device 130 may be operable to initiate a volume preparation mode and start volume acquisition and rendering. For example, the user input device 130 may include a button, an icon on a touchscreen, or any suitable user input device 130 to initiate the volume preparation mode and/or to start volume acquisition and rendering. In a representative embodiment, an operator may provide a freehand drawing of a render start line via the user input device 130. For example, an operator may provide the freehand drawing via a touchscreen, a trackball, a mousing device, or any suitable user input device 130.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a render start line processor 140, a rendering preset processor 150, and a volume rendering processor 160. The signal processor 132 may be capable of receiving input information from a user input device 130 and/or archive 138, generating an output displayable by a display system 134, and manipulating the output in response to input information from a user input device 130, among other things. The signal processor 132, including the render start line processor 140 the rendering preset processor 150, and the volume rendering processor 160, may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a render start line processor 140 that comprises suitable logic, circuitry, interfaces and/or code that may be operable to generate a render box in response to entering a volume preparation mode and receiving a freehand drawing of a render start line. For example, an operator may enter a volume preparation mode using the user input device 130, such as by pressing a 4D button, or any suitable user input device 130. The operator may select a start point on a 2D image, such as by placing a finger or stylus on a touchscreen, or by navigating a cursor/icon presented in a display system 134 using a trackball or mousing device, for example. The operator may manually drag the finger or stylus along the touchscreen along a user-selected path to an end point on the 2D image defined by the operator removing the finger or stylus. Additionally and/or alternatively, the cursor/icon may be navigated from the start point along a user-selected path to an end point defined by the operator pushing a button, for example. The render start line processor 140 may be configured to present a render start line from the start point to the end point along the path traced by the finger, stylus, and/or cursor/icon on the 2D image presented at the display system 134. The render start line processor 140 may be operable to automatically complete the render box by adding sides extending at first ends from the start and end points and a bottom extending between second ends of the sides.

The signal processor 132 may include a rendering preset processor 150 that comprises suitable logic, circuitry, interfaces and/or code that may be operable to analyze pixel intensity values along the render start line and select a set of render mode presets corresponding with one of a plurality of rendering modes based on the pixel intensity values. For example, multiple sets of pre-defined render mode presets may correspond with different render modes, such as a surface rendering mode, a bone rendering mode, a tissue rendering mode, and the like. The sets of render mode presets may be default presets or presets customized and associated with a particular operator, for example. Each of the rendering modes may be associated with a range of pixel intensity values. As an example, a surface rendering mode may be associated with a range of low pixel intensity values. A tissue rendering mode may be associated with a range of medium pixel intensity values. A bone rendering mode may be associate with a range of high pixel intensity values. The rendering preset processor 150 may be operable to analyze the pixels in a region corresponding with the freehand drawing of the render start line. For example, the rendering preset processor 150 may analyze the pixels at and adjacent to the render start line along the path of the render start line between the start and end points of the render start line. The rendering preset processor 150 may determine an average pixel intensity value or a range that a majority of the pixel intensity values fit into, among other things. The rendering preset processor 150 may select one of the plurality of rendering modes based on the corresponding range that fits the pixel intensity values in the region of the render start line. The rendering preset processor 150 may provide the set of render mode presets corresponding with the selected one of the plurality of rendering modes to the volume rendering processor 160.

The signal processor 132 may include a volume rendering processor 160 that comprises suitable logic, circuitry, interfaces and/or code that may be operable to acquire volumetric image data and perform volume rendering on 3D and/or 4D volumes based on the render box defined by the render start line processor 140 and the set of render mode presets selected by the rendering preset processor 150. The volume rendering processor 160 may be used to generate and present volume renderings (e.g., 2D projections) of the volumetric (e.g., 3D and/or 4D) datasets. In this regard, rendering a 2D projection of a 3D and/or 4D dataset may comprise setting or defining a perception angle in space relative to the object being displayed, and then defining or computing necessary information (e.g., opacity and color) for every voxel in the dataset based on the render boxy and set of rendering mode presets. This may be done, for example, using suitable transfer functions for defining RGBA (red, green, blue, and alpha) value for every voxel. The resulting volume rendering may include a depth map correlating a depth value to each pixel in the 2D projection. The volume rendering processor 160 may be operable to present the generated volume rendering at a display system 134 and/or store the generated volume rendering at the archive 138 or any suitable data storage medium.

Figure 3:
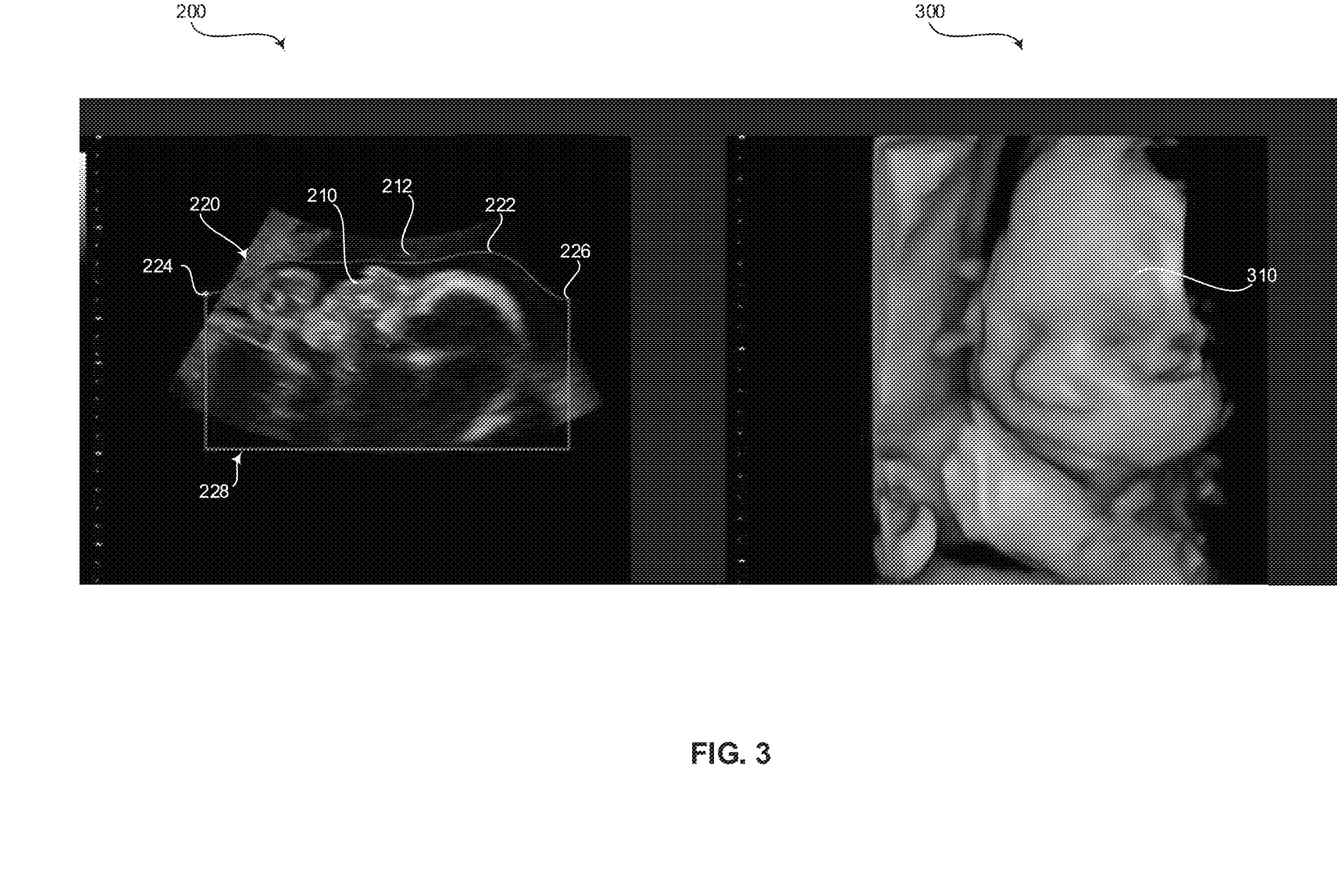
FIG. 3 is an exemplary display of a surface rendering image generated based on a render box having a freehand render start line in a 2D image and automatically selected render mode presets, in accordance with various embodiments.
Figure 4:
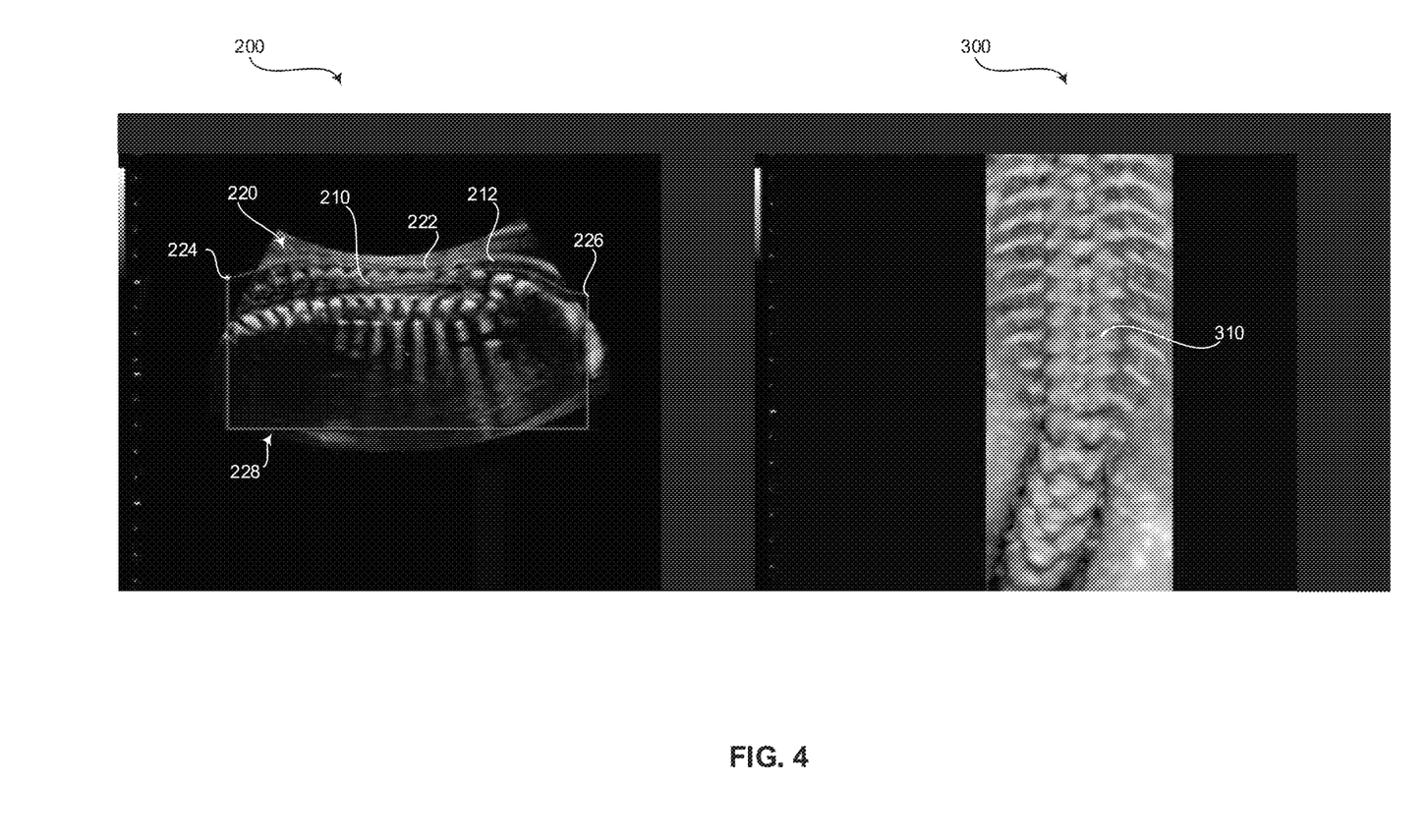
FIG. 4 is an exemplary display of a bone rendering generated based on a render box having a freehand render start line in a 2D image and automatically selected render mode presets, in accordance with various embodiments.
Figure 5:
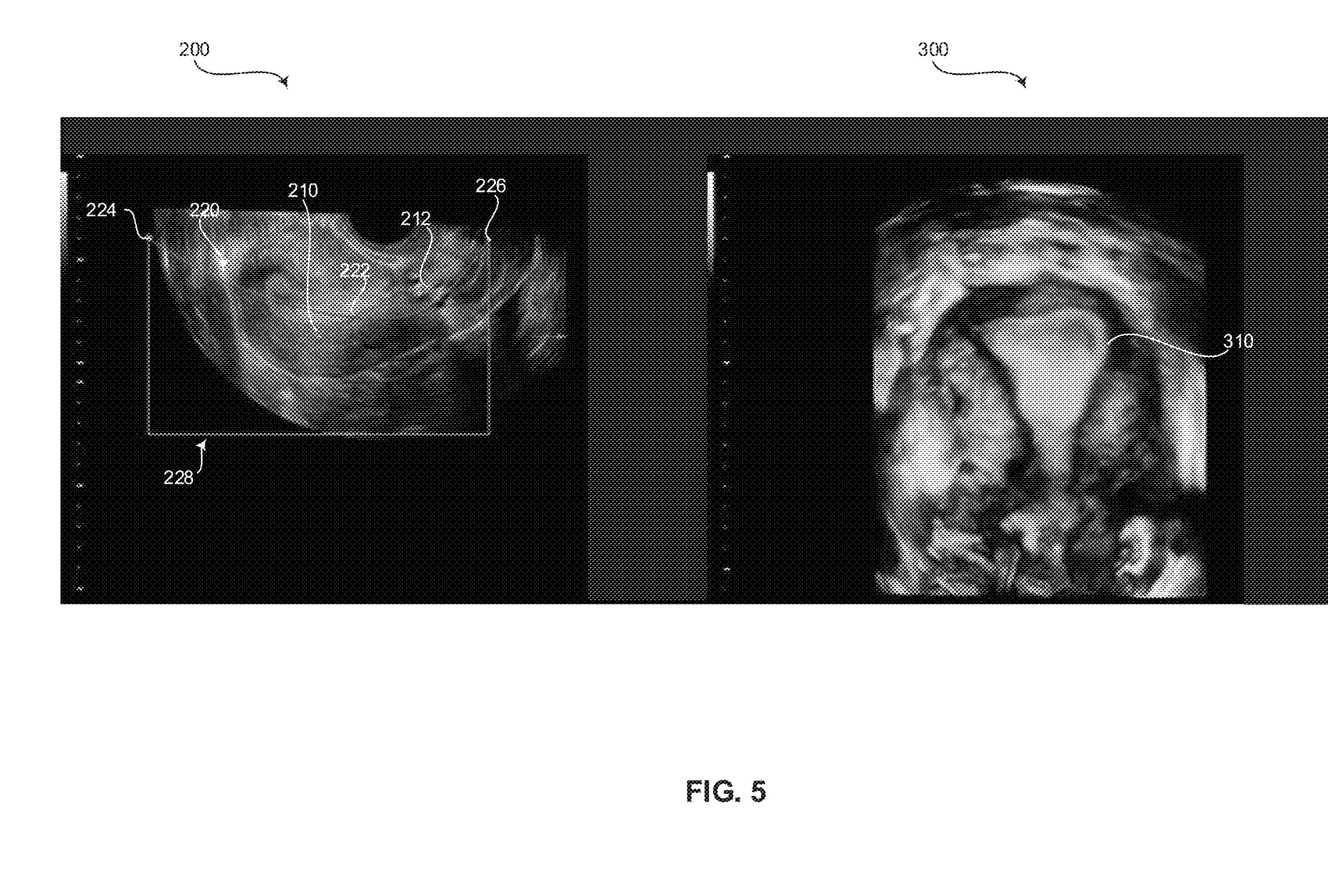
FIG. 5 is an exemplary display of a tissue rendering image generated based on a render box having a freehand render start line in a 2D image and automatically selected render mode presets, in accordance with various embodiments.

FIG. 3 is an exemplary display of a surface rendering image 300 generated based on a render box 220 having a freehand render start line 222 in a 2D image 200 and automatically selected render mode presets, in accordance with various embodiments. FIG. 4 is an exemplary display of a bone rendering image 300 generated based on a render box 220 having a freehand render start line 222 in a 2D image 200 and automatically selected render mode presets, in accordance with various embodiments. FIG. 5 is an exemplary display of a tissue rendering image 300 generated based on a render box 220 having a freehand render start line 222 in a 2D image 200 and automatically selected render mode presets, in accordance with various embodiments. Referring to FIGS. 3-5, volume renderings 300 of a structure of interest 310 are provided. FIG. 3 shows a surface rendering 300 of a fetal face 310. FIG. 4 shows a bone rendering 300 of a spine 310. FIG. 5 shows a tissue rendering 300 of an endometrium of a uterus 310. The volume renderings 300 are generated based on automatically selected render mode presets and a render box 220 in a 2D image 200. Referring again to FIGS. 3-5, the 2D image 200 is a profile of the structure of interest 210. The render box 220 comprises a freehand drawn render start line 222 and a remainder of the box 228. The freehand drawn render start line 222 extends between start and end points 224, 226. The render start line 222 is manually drawn to avoid potential obstructions 212. The automatically generated remainder of the box 228 includes sides extending at first ends from the start and end points 224, 226 and a bottom extending between second ends of the sides. The render box 220 defines the region for volumetric data acquisition and surrounds the structure of interest 210.

Referring again to FIG. 2, the display system 134 may be any device capable of communicating visual information to a user. For example, a display system 134 may include a liquid crystal display, a light emitting diode display, and/or any suitable display or displays. The display system 134 can be operable to display information from the signal processor 132 and/or archive 138, such as 2D images 200, volume renderings 300, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores 2D images, 3D and/or 4D volumes, volume renderings generated by the render volume rendering processor 160, sets of render mode presets corresponding to different rendering mode types, pixel intensity ranges corresponding to different sets of rendering mode presets, instructions for pixel intensity analysis, instructions for selecting a set of render mode presets, instructions for performing volume rendering, and/or instructions for presenting a freehand drawn render start line and automatically completed render box, among other things.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Figure 6:
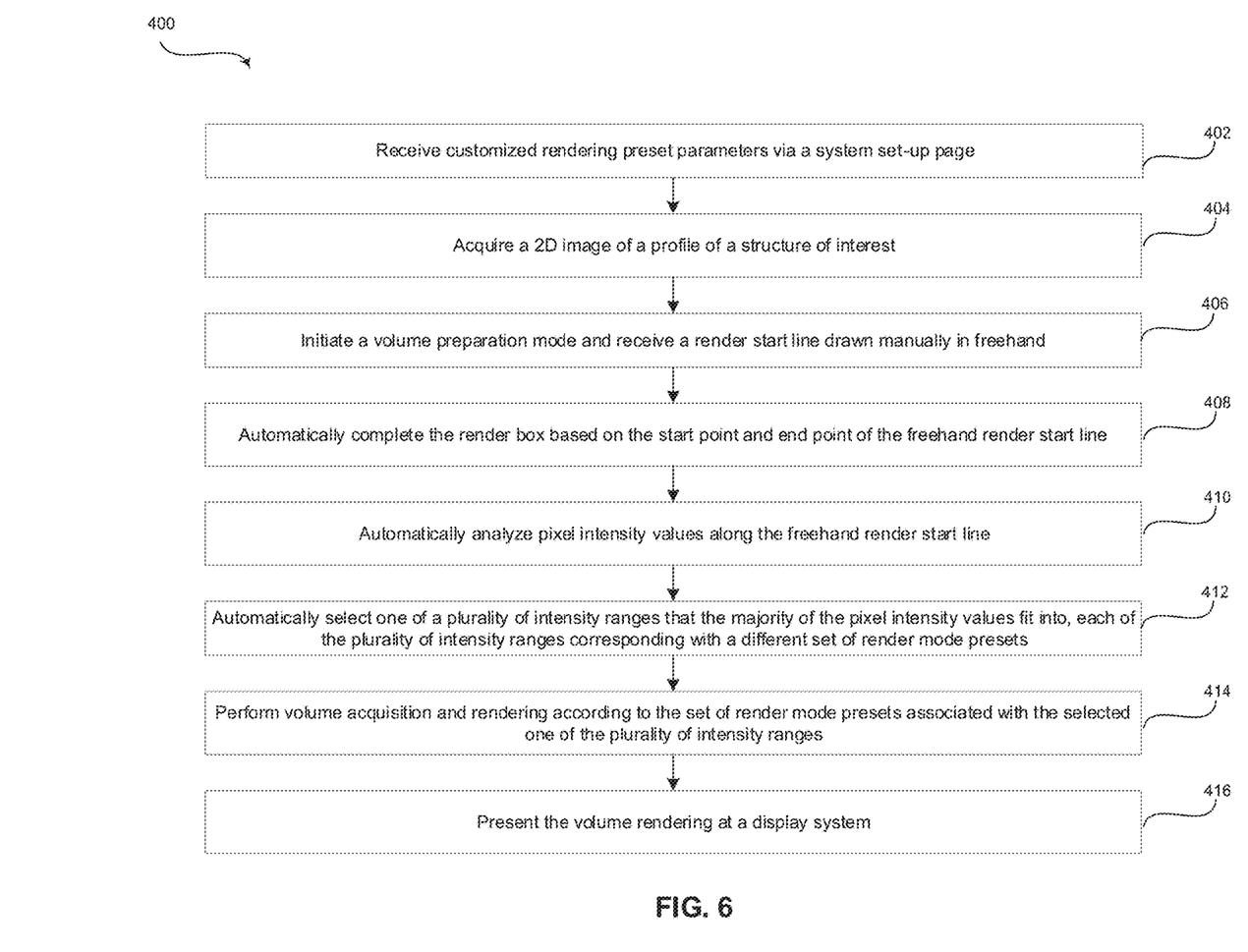
FIG. 6 is a flow chart illustrating exemplary steps that may be utilized for providing freehand render start line drawing tools and automatic render preset selections, in accordance with exemplary embodiments.

FIG. 6 is a flow chart 400 illustrating exemplary steps 402-416 that may be utilized for providing freehand render start line drawing tools and automatic render preset selections, in accordance with exemplary embodiments. Referring to FIG. 4, there is shown a flow chart 400 comprising exemplary steps 402 through 416. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 402, a signal processor 132 of an ultrasound system 100 may receive customized rendering preset parameters via a system set-up page. For example, the system 100 may include sets of default render presets each corresponding to a different rendering mode. In various embodiments, an operator may choose to alter one or more of the sets of default render presets. For example, an operator may provide instructions via a user input device 130 to a signal processor 132 to change the default render color of HD life corresponding to the surface rendering mode to sepia. An another example, the operator may provide instructions via the user input device 130 to a signal processor 132 to change the bone rendering mode from a mix of an X-ray render mode and a maximum transparency mode to a mix of surface texture rendering mode and the maximum transparency mode. Additionally, the operator may provide instructions via the user input device 130 to a signal processor 132 to change the percentage mix of 50% surface texture render mode and 50% X-ray mode of the tissue rendering mode to 60% surface texture render mode and 40% X-ray mode. In certain embodiments, step 402 may be omitted if customized rendering presets are not desired or available.

At step 404, the ultrasound system 100 may acquire a 2D image 200 of a profile of a structure of interest 210. For example, an operator may manipulate an ultrasound probe 104 of the ultrasound system 100 to obtain a desired profile view of a structure of interest 210, such as a fetal head, spine, endometrium of a uterus, or any suitable structure. The 2D image 200 may be presented by the signal processor 132 at a display system 134.

At step 406, the signal processor 132 of the ultrasound system 100 may initiate a volume preparation mode and receive a render start line 220 drawn manually in freehand. For example, a render start line processor 140 of the signal processor 132 may receive an instruction via the user input device 130 to initiate a volume preparation mode, such as the depression of a button or any suitable instruction provided via a user input device 130. The render start line processor 140 may receive a traced path over the 2D image of the render start line 220 from a start point 224 to an end point 226. The start point 224, end point 226, and path 222 may be provided via a user input device 130, such as a finger or stylus dragged across a touchscreen, or a trackball or mousing device navigating a cursor/icon across the 2D image 200, for example. The render start line processor 140 may present the render start line 222 as it is drawn overlaid on the 2D image 200 at the display system 134. The render start line 222 may be manually drawn to avoid obstructions 212 in the 2D image 200, for example.

At step 408, the signal processor 132 of the ultrasound system 100 may automatically complete the render box 220 based on the start point 224 and end point 226 of the freehand render start line 222. For example, the render start line processor 140 may automatically generate a remainder 228 of the box 220 by adding sides extending at first ends from the start and end points 224, 226 of the render start line 222 and a bottom extending between second ends of the sides.

At step 410, the signal processor 132 may automatically analyze pixel intensity values along the freehand render start line 222. For example, a rendering preset processor 150 of the signal processor 132 may be operable to analyze the pixels in a region corresponding with the freehand drawing of the render start line 222. As an example, the rendering preset processor 150 may analyze the pixels at and adjacent to the render start line 222 along the path of the render start line between the start and end points 224, 226 of the render start line 222. The rendering preset processor 150 may determine an average pixel intensity value or a range that a majority of the pixel intensity values fit into, among other things.

At step 412, the signal processor 132 may automatically select one of a plurality of intensity ranges that the majority of the pixel intensity values fit into, each of the plurality of intensity ranges corresponding with a different set of render mode presets. For example, the rendering preset processor 150 may select one of a plurality of ranges of intensity values that correspond with one of a plurality of rendering modes based on the pixel intensity values. In various embodiments, multiple sets of pre-defined render mode presets may correspond with different render modes, such as a surface rendering mode, a bone rendering mode, a tissue rendering mode, and the like. Each of the rendering modes may be associated with a range of pixel intensity values. The rendering preset processor 150 may select one of the plurality of rendering modes based on the corresponding range that fits the pixel intensity values in the region of the render start line 222. The rendering preset processor 150 may provide the set of render mode presets corresponding with the selected one of the plurality of rendering modes to the volume rendering processor 160.

At step 414, the signal processor 132 may perform volume acquisition and rendering according to the set of render mode presets associated with the selected one of the plurality of intensity ranges. For example, a volume rendering processor 160 of the signal processor 132 may control the ultrasound system 100 to acquire 3D and/or 4D volumes with an ultrasound probe 104 based on the render box 220 and the set of render mode presets associated with the selected one of the plurality of intensity ranges. The ultrasound probe 104 may provide the acquired 3D and/or 4D volumes to the signal processor 132. The volume rendering processor 160 of the signal processor 132 may render the 3D and/or 4D volumes according to the set of render mode presets associated with the selected one of the plurality of intensity ranges.

At step 416, the signal processor 132 may present the volume rendering at a display system 134. For example, the volume rendering processor 160 of the signal processor 132 may present the volume rendering generated at step 414 at the display system 134 of the ultrasound system 100.

Aspects of the present disclosure provide a method 400 and system 100, 200 for providing freehand render start line drawing tools and automatic render preset selections. In accordance with various embodiments, the method 400 may comprise receiving 406, by at least one processor 132, 140, a render start line 222 drawn in freehand via a user input device 130 on a two-dimensional (2D) image 200 of a profile of a structure of interest 210. The method 400 may comprise analyzing 410, by the at least one processor 132, 150, pixel intensity values in a region of the render start line 222. The method 400 may comprise automatically selecting 412, by the at least one processor 132, 150, a set of render mode presets from a plurality of sets of render mode presets based on the pixel intensity values in the region of the render start line 222. Each of the plurality of sets of render mode presets may be associated with a different one of a plurality of rendering modes. Each of the plurality of rendering modes may be associated with a different one of a plurality of pixel intensity value ranges. The method 400 may comprise generating 414, by the at least one processor 132, 160, a volume rendering 300 according to the automatically selected set of render mode presets. The method 400 may comprise presenting 416, by the at least one processor, the volume rendering 300 at a display system 134.

In an exemplary embodiment, the method 400 may comprise receiving 402, by the at least one processor 132, customization of at least one of the plurality of sets of render mode presets at a system set-up page via the user input device 130. In a representative embodiment, the method 400 may comprise acquiring 404, via an ultrasound system 100, the 2D image 200 of the profile of the structure of interest 210. In certain embodiments, the method 400 may comprise automatically completing 408, by the at least one processor 132, 140, a render box 220 based on a start point 224 and an end point 226 of the render start line 222. In various embodiments, the method 400 may comprise performing 414, via an ultrasound system 100, a volume acquisition based on the render box 220 and the automatically selected set of render mode presets. In an exemplary embodiment, the plurality of rendering modes may comprise a surface rendering mode associated with a first one of the plurality of pixel intensity ranges. The plurality of rendering modes may comprise a tissue rendering mode associated with a second one of the plurality of pixel intensity ranges. The plurality of rendering modes may comprise a bone rendering mode associated with a third one of the plurality of pixel intensity ranges. Second pixel intensity values in the second one of the plurality of pixel intensity ranges may be greater than first pixel values in the first one of the plurality of pixel intensity ranges. Third pixel intensity values in the third one of the plurality of pixel intensity ranges may be greater than the second pixel values in the second one of the plurality of pixel intensity ranges. In a representative embodiment, the user input device 130 that provides the render start line 222 drawn in freehand may be a touchscreen. In certain embodiments, the user input device 130 that provides the render start line drawn 222 in freehand may be one of a mousing device or a trackball.

Various embodiments provide a system 100 for providing freehand render start line drawing tools and automatic render preset selections. The system 100 may comprise a user input device 130, at least one processor 132, 140, 150, 160, and a display system 134. The user input device 130 may be configured to provide a render start line 222 drawn in freehand on a two-dimensional (2D) image 200 of a profile of a structure of interest 210. The at least one processor 132, 140 may be configured to receive the render start line 222. The at least one processor 132, 150 may be configured to analyze pixel intensity values in a region of the render start line 222. The at least one processor 132, 150 may be configured to automatically select a set of render mode presets from a plurality of sets of render mode presets based on the pixel intensity values in the region of the render start line 222. Each of the plurality of sets of render mode presets may be associated with a different one of a plurality of rendering modes. Each of the plurality of rendering modes may be associated with a different one of a plurality of pixel intensity value ranges. The at least one processor 132, 160 may be configured to perform volume rendering according to the automatically selected set of render mode presets. The display system 134 may be configured to display the volume rendering 300.

In a representative embodiment, the system 100 may comprise an ultrasound system 100 operable to acquire the 2D image 200 of the profile of the structure of interest 210. In certain embodiments, the at least one processor 132, 140 may be configured to automatically complete a render box 220 based on a start point 224 and an end point 226 of the render start line 222. In various embodiments, the system 100 may comprise an ultrasound system 100 operable to perform a volume acquisition based on the render box 220 and the automatically selected set of render mode presets. In certain embodiments, the plurality of rendering modes may comprise a surface rendering mode associated with a first one of the plurality of pixel intensity ranges. The plurality of rendering modes may comprise a tissue rendering mode associated with a second one of the plurality of pixel intensity ranges. The plurality of rendering modes may comprise a bone rendering mode associated with a third one of the plurality of pixel intensity ranges. Second pixel intensity values in the second one of the plurality of pixel intensity ranges may be greater than first pixel values in the first one of the plurality of pixel intensity ranges. Third pixel intensity values in the third one of the plurality of pixel intensity ranges may be greater than the second pixel values in the second one of the plurality of pixel intensity ranges. In an exemplary embodiment, the user input device 130 that provides the render start line 222 drawn in freehand may be a touchscreen. In a representative embodiment, the user input device 130 that provides the render start line drawn in freehand may be one of a mousing device or a trackball.

Certain embodiments provide a non-transitory computer readable medium having stored thereon, a computer program having at least one code section. The at least one code section is executable by a machine for causing the machine to perform steps 400. The steps 400 may comprise presenting 402 a volume rendering 302 of an object having an initial view at a display system 134. The steps 400 may comprise receiving 406 a render start line 222 drawn in freehand via a user input device 130 on a two-dimensional (2D) image 200 of a profile of a structure of interest 210. The steps 400 may comprise analyzing 410 pixel intensity values in a region of the render start line 222. The steps 400 may comprise automatically selecting 412 a set of render mode presets from a plurality of sets of render mode presets based on the pixel intensity values in the region of the render start line 222. Each of the plurality of sets of render mode presets may be associated with a different one of a plurality of rendering modes. Each of the plurality of rendering modes may be associated with a different one of a plurality of pixel intensity value ranges. The steps 400 may comprise generating 414 a volume rendering 310 according to the automatically selected set of render mode presets. The steps 400 may comprise presenting 416 the volume rendering 310 at a display system 134.

In various embodiments, the steps 400 may comprise receiving 402 customization of at least one of the plurality of sets of render mode presets at a system set-up page via the user input device 130. In an exemplary embodiment, steps 400 may comprise automatically completing 408 a render box 220 based on a start point 224 and an end point 226 of the render start line 222. In a representative embodiment, the plurality of rendering modes may comprise a surface rendering mode associated with a first one of the plurality of pixel intensity ranges. The plurality of rendering modes may comprise a tissue rendering mode associated with a second one of the plurality of pixel intensity ranges. The plurality of rendering modes may comprise a bone rendering mode associated with a third one of the plurality of pixel intensity ranges. Second pixel intensity values in the second one of the plurality of pixel intensity ranges may be greater than first pixel values in the first one of the plurality of pixel intensity ranges. Third pixel intensity values in the third one of the plurality of pixel intensity ranges may be greater than the second pixel values in the second one of the plurality of pixel intensity ranges. In certain embodiments, the user input device 130 that provides the render start line 222 drawn in freehand is a touchscreen.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing freehand render start line drawing tools and automatic render preset selections.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
   receiving, by at least one processor, a render start line drawn in freehand via a user input device on a two-dimensional (2D) image of a profile of a structure of interest;
   automatically completing, by the at least one processor, a render box based on a start point and an end point of the render start line, wherein the render start line is one side of the render box;
   analyzing, by the at least one processor, pixel intensity values in a region of the render start line;
   automatically selecting, by the at least one processor, a set of render mode presets from a plurality of sets of render mode presets based on the pixel intensity values in the region of the render start line, each of the plurality of sets of render mode presets associated with a different one of a plurality of rendering modes, each of the plurality of rendering modes associated with a different one of a plurality of pixel intensity value ranges;
   generating, by the at least one processor, a volume rendering according to the automatically selected set of render mode presets, wherein the volume rendering is a 2D projection of a three-dimensional (3D) or four-dimensional (4D) image data set; and
   presenting, by the at least one processor, the volume rendering at a display system.

2. The method of claim 1, comprising receiving, by the at least one processor, customization of at least one of the plurality of sets of render mode presets at a system set-up page via the user input device.

3. The method of claim 1, comprising acquiring, via an ultrasound system, the 2D image of the profile of the structure of interest.

4. The method of claim 1, comprising performing, via an ultrasound system, a volume acquisition of the 3D or 4D image data set.

5. The method of claim 4, wherein the volume acquisition is based on the render box and the automatically selected set of render mode presets.

6. The method of claim 1, wherein the plurality of rendering modes comprise:
- a surface rendering mode associated with a first one of the plurality of pixel intensity ranges;
- a tissue rendering mode associated with a second one of the plurality of pixel intensity ranges; and
- a bone rendering mode associated with a third one of the plurality of pixel intensity ranges,
- wherein second pixel intensity values in the second one of the plurality of pixel intensity ranges is greater than first pixel values in the first one of the plurality of pixel intensity ranges, and
- wherein third pixel intensity values in the third one of the plurality of pixel intensity ranges is greater than the second pixel values in the second one of the plurality of pixel intensity ranges.

7. The method of claim 1, wherein the user input device that provides the render start line drawn in freehand is a touchscreen.

8. The method of claim 1, wherein the user input device that provides the render start line drawn in freehand is one of a mousing device or a trackball.

9. A system comprising:
- a user input device configured to provide a render start line drawn in freehand on a two-dimensional (2D) image of a profile of a structure of interest;
- at least one processor configured to:
  - receive the render start line;
  - automatically complete a render box based on a start point and an end point of the render start line, wherein the render start line is one side of the render box;
  - analyze pixel intensity values in a region of the render start line;
  - automatically select a set of render mode presets from a plurality of sets of render mode presets based on the pixel intensity values in the region of the render start line, each of the plurality of sets of render mode presets associated with a different one of a plurality of rendering modes, each of the plurality of rendering modes associated with a different one of a plurality of pixel intensity value ranges; and
  - generate a volume rendering according to the automatically selected set of render mode presets, wherein the volume rendering is a 2D projection of a three-dimensional (3D) or four-dimensional (4D) image data set; and
- a display system configured to display the volume rendering.

10. The system of claim 9, comprising an ultrasound system operable to acquire the 2D image of the profile of the structure of interest.

11. The system of claim 9, comprising an ultrasound system operable to perform a volume acquisition of the 3D or 4D image data set.

12. The system of claim 11, wherein the volume acquisition is based on the render box and the automatically selected set of render mode presets.

13. The system of claim 9, wherein the plurality of rendering modes comprise:
- a surface rendering mode associated with a first one of the plurality of pixel intensity ranges;
- a tissue rendering mode associated with a second one of the plurality of pixel intensity ranges; and
- a bone rendering mode associated with a third one of the plurality of pixel intensity ranges,
- wherein second pixel intensity values in the second one of the plurality of pixel intensity ranges is greater than first pixel values in the first one of the plurality of pixel intensity ranges, and
- wherein third pixel intensity values in the third one of the plurality of pixel intensity ranges is greater than the second pixel values in the second one of the plurality of pixel intensity ranges.

14. The system of claim 9, wherein the user input device that provides the render start line drawn in freehand is a touchscreen.

15. The system of claim 9, wherein the user input device that provides the render start line drawn in freehand is one of a mousing device or a trackball.

16. A non-transitory computer readable medium having stored thereon, a computer program having at least one code section, the at least one code section being executable by a machine for causing the machine to perform steps comprising:
- receiving a render start line drawn in freehand via a user input device on a two-dimensional (2D) image of a profile of a structure of interest;
- automatically completing a render box based on a start point and an end point of the render start line, wherein the render start line is one side of the render box;
- analyzing pixel intensity values in a region of the render start line;
- automatically selecting a set of render mode presets from a plurality of sets of render mode presets based on the pixel intensity values in the region of the render start line, each of the plurality of sets of render mode presets associated with a different one of a plurality of rendering modes, each of the plurality of rendering modes associated with a different one of a plurality of pixel intensity value ranges;
- generating a volume rendering according to the automatically selected set of render mode presets, wherein the volume rendering is a 2D projection of a three-dimensional (3D) or four-dimensional (4D) image data set; and
- presenting the volume rendering at a display system.

17. The non-transitory computer readable medium of claim 16, comprising receiving customization of at least one of the plurality of sets of render mode presets at a system set-up page via the user input device.

18. The non-transitory computer readable medium of claim 16, comprising receiving a volume acquisition of the 3D or 4D image data set.

19. The non-transitory computer readable medium of claim 16, wherein the plurality of rendering modes comprise:
- a surface rendering mode associated with a first one of the plurality of pixel intensity ranges;
- a tissue rendering mode associated with a second one of the plurality of pixel intensity ranges; and
- a bone rendering mode associated with a third one of the plurality of pixel intensity ranges,
- wherein second pixel intensity values in the second one of the plurality of pixel intensity ranges is greater than first pixel values in the first one of the plurality of pixel intensity ranges, and
- wherein third pixel intensity values in the third one of the plurality of pixel intensity ranges is greater than the second pixel values in the second one of the plurality of pixel intensity ranges.

20. The non-transitory computer readable medium of claim 16, wherein the user input device that provides the render start line drawn in freehand is a touchscreen.

\* \* \* \* \*